United States Patent
Pedrotti et al.

(10) Patent No.: US 6,917,754 B2
(45) Date of Patent: Jul. 12, 2005

(54) MULTI-FUNCTIONAL ELECTRICAL VAPORIZER FOR A LIQUID SUBSTANCE AND METHOD OF MANUFACTURING SUCH A VAPORIZER

(75) Inventors: Andrea Pedrotti, Pietromurata (IT); Franco Zobele, Trento (IT); Paolo Campedelli, Mori (IT); Stefano Baldessari, Caldonazzo (IT)

(73) Assignee: S.C. Johnson & Son, Inc., Racine, WI (US)

( * ) Notice: Subject to any disclaimer, the term of this patent is extended or adjusted under 35 U.S.C. 154(b) by 69 days.

(21) Appl. No.: 10/212,746

(22) Filed: Aug. 7, 2002

(65) Prior Publication Data

US 2003/0063902 A1 Apr. 3, 2003

(30) Foreign Application Priority Data

Aug. 7, 2001 (EP) .............................. 01830528

(51) Int. Cl.[7] ................................................. F24F 6/08
(52) U.S. Cl. ...................................... 392/395; 392/392
(58) Field of Search .............................. 392/386, 387, 392/390, 392, 393, 395; 122/366; 239/34, 44, 45, 135, 136

(56) References Cited

U.S. PATENT DOCUMENTS

| | | | |
|---|---|---|---|
| 2,472,992 A | | 6/1949 | Szekely |
| 2,611,068 A | * | 9/1952 | Wellens ...................... 392/392 |
| 2,828,953 A | | 4/1958 | Hartmann |
| 3,747,902 A | | 7/1973 | Bailey .......................... 261/30 |
| 3,780,260 A | | 12/1973 | Eisner ......................... 219/271 |
| 3,804,592 A | | 4/1974 | Garbe .......................... 21/121 |
| 3,872,280 A | | 3/1975 | Van Dalen .................. 219/271 |
| 3,948,445 A | | 4/1976 | Andeweg ..................... 239/53 |
| 4,621,768 A | * | 11/1986 | Lhoste et al. ................. 239/44 |
| 4,968,487 A | | 11/1990 | Yamamoto et al. .......... 422/125 |
| 5,038,394 A | * | 8/1991 | Hasegawa et al. .......... 392/395 |
| 5,081,104 A | | 1/1992 | Orson, Sr. ...................... 512/3 |
| 5,095,647 A | | 3/1992 | Zobele et al. ................. 43/125 |
| 5,114,625 A | | 5/1992 | Gibson ........................ 261/30 |
| 5,222,186 A | * | 6/1993 | Schimanski et al. ........ 392/395 |
| 5,290,546 A | | 3/1994 | Hasegawa et al. ......... 424/76.2 |
| 5,402,517 A | | 3/1995 | Gillett et al. ............... 392/386 |
| 5,484,086 A | | 1/1996 | Pu .............................. 222/187 |
| 5,601,636 A | | 2/1997 | Glucksman .................... 96/63 |
| 5,647,053 A | | 7/1997 | Schroeder et al. .......... 392/390 |
| 5,932,147 A | | 8/1999 | Chen ........................... 261/30 |

(Continued)

FOREIGN PATENT DOCUMENTS

| | | |
|---|---|---|
| EP | 0 976 410 | 12/1998 |
| EP | 0 962 132 | 1/1999 |
| EP | 0 943 344 | 3/1999 |
| ES | 1 005 422 | 11/1998 |
| WO | WO 98/19526 | 5/1998 |
| WO | WO 98/46284 | 10/1998 |
| WO | WO 02/26274 | 4/2002 |

*Primary Examiner*—Sang Y. Paik

(57) ABSTRACT

A multi-functional electrical vaporizer for a liquid substance includes a bottle for holding the liquid substance, a wick for drawing the liquid substance out of the bottle, an electrical heating device positioned proximate to an upper portion of the wick, an electrical plug assembly, an electrical circuit for powering the electrical heating device, a housing structure with respect to which the bottle is detachably secured and in which at least the electrical plug assembly, the electrical circuit, and the electrical heating device are disposed, and a cover that is joined to and at least partially covers the housing structure. The housing structure, which includes a first shell and a second shell that are joined together, is configured to receive any of a plurality of different additional functional devices. The cover is provided with at least one access window corresponding to whatever additional functional device the housing structure is to be equipped with.

19 Claims, 12 Drawing Sheets

U.S. PATENT DOCUMENTS

| | | | |
|---|---|---|---|
| 6,104,867 A | 8/2000 | Stathakis et al. | 392/403 |
| 6,145,241 A | 11/2000 | Okuno | 43/129 |
| 6,278,840 B1 | 8/2001 | Basaganas Millan | 392/390 |
| 6,285,830 B1 * | 9/2001 | Basaganas Millan | 392/395 |
| 6,361,752 B1 * | 3/2002 | Demarest et al. | 422/306 |
| 6,413,302 B1 | 7/2002 | Harrison et al. | 96/63 |
| 6,446,583 B2 | 9/2002 | Vieira | 122/366 |
| 6,466,739 B2 * | 10/2002 | Ambrosi et al. | 392/395 |
| 2002/0021892 A1 | 2/2002 | Ambrosi et al. | 392/395 |

* cited by examiner

MULTI-FUNCTIONAL ELECTRICAL VAPORIZER FOR A LIQUID SUBSTANCE AND METHOD OF MANUFACTURING SUCH A VAPORIZER

BACKGROUND OF THE INVENTION

1. Field of the Invention

Our invention relates generally to an electrical vaporizer for a liquid substance, such as an aromatic liquid, an insecticide, or the like. In particular, our invention relates to a multi-functional vaporizer that, in addition to performing the basic function of vaporizing the liquid substance by means of an electrical heating device, can also be equipped with one or more additional functional devices, such as a draft regulator, a wick adjustment mechanism, a fan, a night light, an indicator light, a programmable user interface, or the like.

2. Description of the Related Art

The worldwide market for electrical vaporizers for use with aromatic liquids, insecticides, and the like is extremely diverse both with respect to the technical specifications of the electrical components of the vaporizer and with respect to the functional capabilities demanded by users. Such diversity in the marketplace causes considerable problems for the manufacturers of these vaporizers, who, on the one hand, must produce different models tailored to meet the specific requirements of each market, yet, on the other hand, are under considerable pressure to reduce production costs in order to keep pace with their competitors.

As for the technical specifications of the electrical components, the problem does not lie so much in the safety standards of the components, because it is sufficient to adopt for all markets the most stringent regulations from among all the countries in which the vaporizer will be sold. Indeed, the savings that result from producing substantially homogeneous electrical components easily offset any increased costs of using higher quality components than may strictly be necessary.

Rather, a more difficult problem for manufacturers has to do with the varying market preferences as to which additional functional capabilities the vaporizer should be equipped with. In developing countries, for example, consumers typically want vaporizers capable of performing only very basic functions, such as heating, and possibly a few other simple features, such as an on/off indicator light, an on/off switch, or an extra electrical socket for replacing the one occupied by the vaporizer. In more advanced or wealthier countries, consumers typically want more complex vaporizers that are equipped with, for example, a fan, a programmable user interface, a night light, or other more sophisticated features.

Aesthetic appearance is also an important issue with vaporizers, especially wall-mounted ones that are often visibly displayed in one's home or place of work. But while the external appearance of vaporizers should be designed to meet current market preferences, such appearance should be easily and inexpensively modifiable, so that manufacturers (and also consumers) can keep up with the constantly evolving market trends.

Prior to our invention, the response of vaporizer manufacturers has been to produce and store in inventory a very large number of devices which vary from each other, not only with respect to the intrinsic technical characteristics of each device, but also with respect to the various additional features and aesthetic appearance of the device. Producing and maintaining large inventories, however, prevents manufacturers from reducing their production costs and creates a formidable barrier to further market expansion.

SUMMARY OF THE INVENTION

In conceiving our invention, we realized that the foregoing problem could be addressed only by radically departing from the conventional wisdom of producing and maintaining large inventories of diverse devices, and, instead, developing a new line of vaporizers having a universal core housing structure that can easily accommodate any of several different functional devices and external designs.

In one aspect, our invention relates to a multi-functional electrical vaporizer for a liquid substance. The vaporizer includes (i) a bottle for holding the liquid substance, (ii) a wick for drawing the liquid substance out of the bottle, the wick having a lower portion disposed within the bottle and an upper portion extending out of the bottle, (iii) an electrical heating device positioned proximate to the upper portion of the wick, (iv) an electrical plug assembly, (v) an electrical circuit, connected between the electrical plug assembly and the electrical heating device, for powering the electrical heating device, (vi) a housing structure with respect to which the bottle is detachably secured and in which at least the electrical plug assembly, the electrical circuit, and the electrical heating device are disposed, and (vii) a cover that is joined to and at least partially covers the housing structure. The housing structure includes a first shell and a second shell that are joined together, and is configured to receive any of a plurality of different additional functional devices. Meanwhile, the cover is provided with at least one access window corresponding to whatever additional functional device the housing structure is to be equipped with.

In another aspect, our invention relates to a multi-functional electrical vaporizer for dispersing a liquid substance contained in a bottle provided with a wick for drawing the liquid substance out of the bottle and toward an upper portion of the wick. The vaporizer includes (i) an electrical heating device for being positioned proximate to the upper portion of the wick, (ii) an electrical plug assembly, (iii) an electrical circuit, connected between the electrical plug assembly and the electrical heating device, for powering the electrical heating device, (iv) a housing structure in which at least the electrical plug assembly, the electrical circuit, and the electrical heating device are disposed, the housing structure including a first shell and a second shell that are joined together, the housing structure being configured to receive any of a plurality of different additional functional devices, (v) at least one additional functional device disposed within the housing structure, and (vi) a cover that is joined to and at least partially covers the housing structure, the cover including at least one access window corresponding to the additional functional device the housing structure is equipped with. The additional functional device is selected from among the following: (a) a draft regulator, (b) a wick adjustment mechanism for displacing the wick relative to the electrical heating device, (c) a fan, (d) a night light, (e) an indicator light, and (f) a programmable user interface.

In yet another aspect, our invention relates to a method of manufacturing an electrical vaporizer for a liquid substance. The method includes at least the following steps: (i) forming a housing structure including joinable first and second shells, the housing structure being configured to receive any of a plurality of different additional functional devices, (ii)

disposing within the housing structure an electrical plug assembly, an electrical heating device, and an electrical circuit that is connected between the electrical plug assembly and the electrical heating device, (iii) equipping the housing structure with at least one of the additional functional devices, and (iv) providing a cover for at least part of the housing structure, the cover including at least one access window corresponding to the additional functional device the housing structure is equipped with.

A better understanding of these and other features and advantages of the invention may be had by reference to the drawings and to the accompanying description, in which preferred embodiments of the invention are illustrated and described.

BRIEF DESCRIPTION OF THE DRAWINGS

Throughout the figures, like or corresponding reference numerals and/or characters have been used for like or corresponding parts.

DESCRIPTION OF THE PREFERRED EMBODIMENTS

FIGS. 1–7 illustrate a vaporizer according to a first preferred embodiment of our invention. The vaporizer includes a first shell 1 and a second shell 2 that can be joined together in any well-known manner, including rivets, screws, heat-staking, or the like. The first and second shells 1 and 2 together form the core housing structure of the vaporizer. The housing structure contains many of the basic functional components of the vaporizer, as well as one or more additional functional devices. Basic components of the vaporizer include a rotatable electrical plug assembly S, a contact carrier M having several electrical contacts, an electrical heating device R connected to a pair of contacts $M_R$ of the contact carrier M, a bottle F containing the liquid substance to be evaporated, and a wick W for drawing the liquid substance out of the bottle and toward an upper portion of the wick.

The plug assembly S is of the sliding-contact type and has contacts $S_M$ for engagement with either of two possible corresponding pairs of contacts $M_S$ on the contact carrier M. The pairs of contacts $M_S$ on the contact carrier M are mutually offset by 90°, allowing the plug to be rotated through a range of 360°. This makes the vaporizer easily adaptable for use in both horizontal and vertical electrical sockets, as are found in different parts of the world.

The vaporizer is completed by a cover 3, which preferably surrounds substantially the entire outer surface of the second shell 2 such that substantially only the cover is visible when looking at the vaporizer head-on. The cover 3 is joined to the housing structure, preferably to the second shell 2, by any suitable fastening means. The cover 3 includes one or more access windows corresponding to whatever additional functional device(s) the vaporizer is equipped with. Apart from these minimal functional considerations, the cover design may be tailored to meet consumers' aesthetic preferences.

An advantageous feature of our invention is that it permits any of several different additional functional devices to be incorporated in the vaporizer, without requiring any substantial modification to either the core housing structure or the basic functional components of the vaporizer. To that end, the housing structure, in advance, is configured to receive any of the additional functional devices. The design of the cover 3, meanwhile, can be varied depending on the additional functional device(s) that the vaporizer is equipped with and the aesthetic preferences of a particular market. Additional functional devices for the vaporizer may include, for example, a draft regulator, a wick adjustment mechanism, a fan, a night light, an indicator light, a programmable user interface, or the like.

Figure 2:
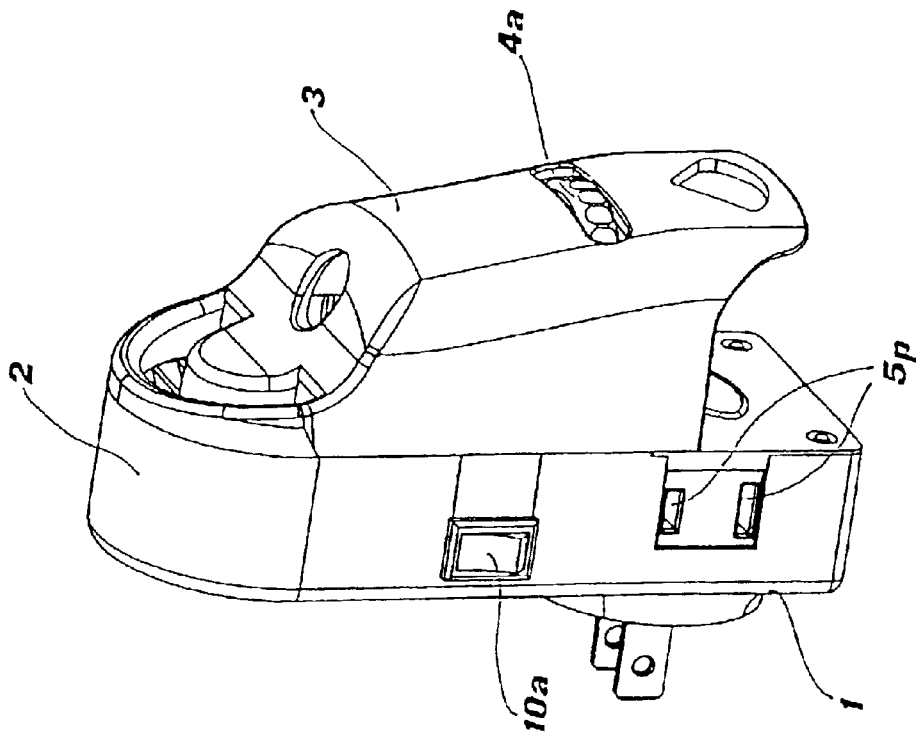
FIGS. 1 and 2 are, respectively, rear and front perspective views of a vaporizer according to a first preferred embodiment of our invention.
Figure 1:
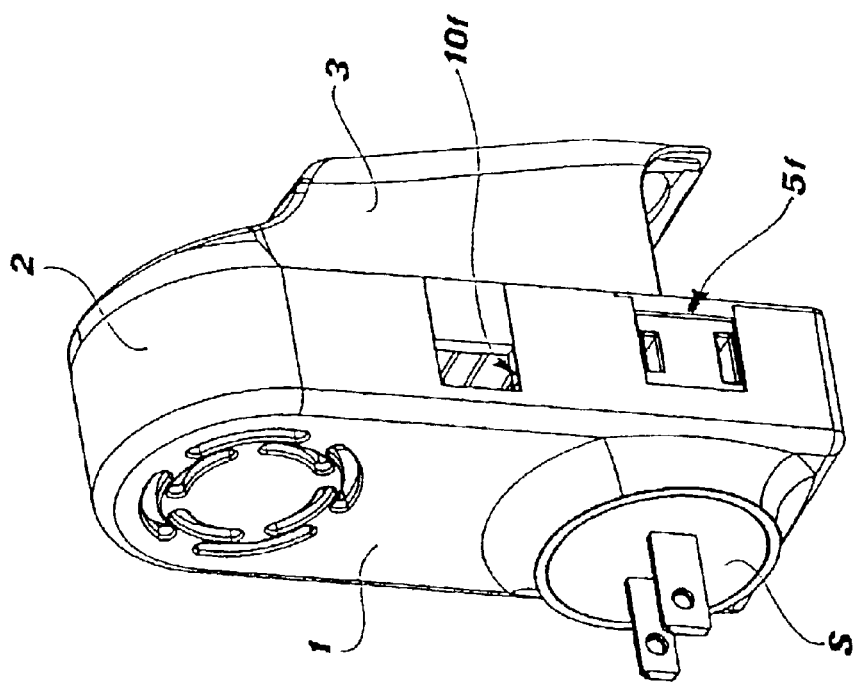
Figure 3:
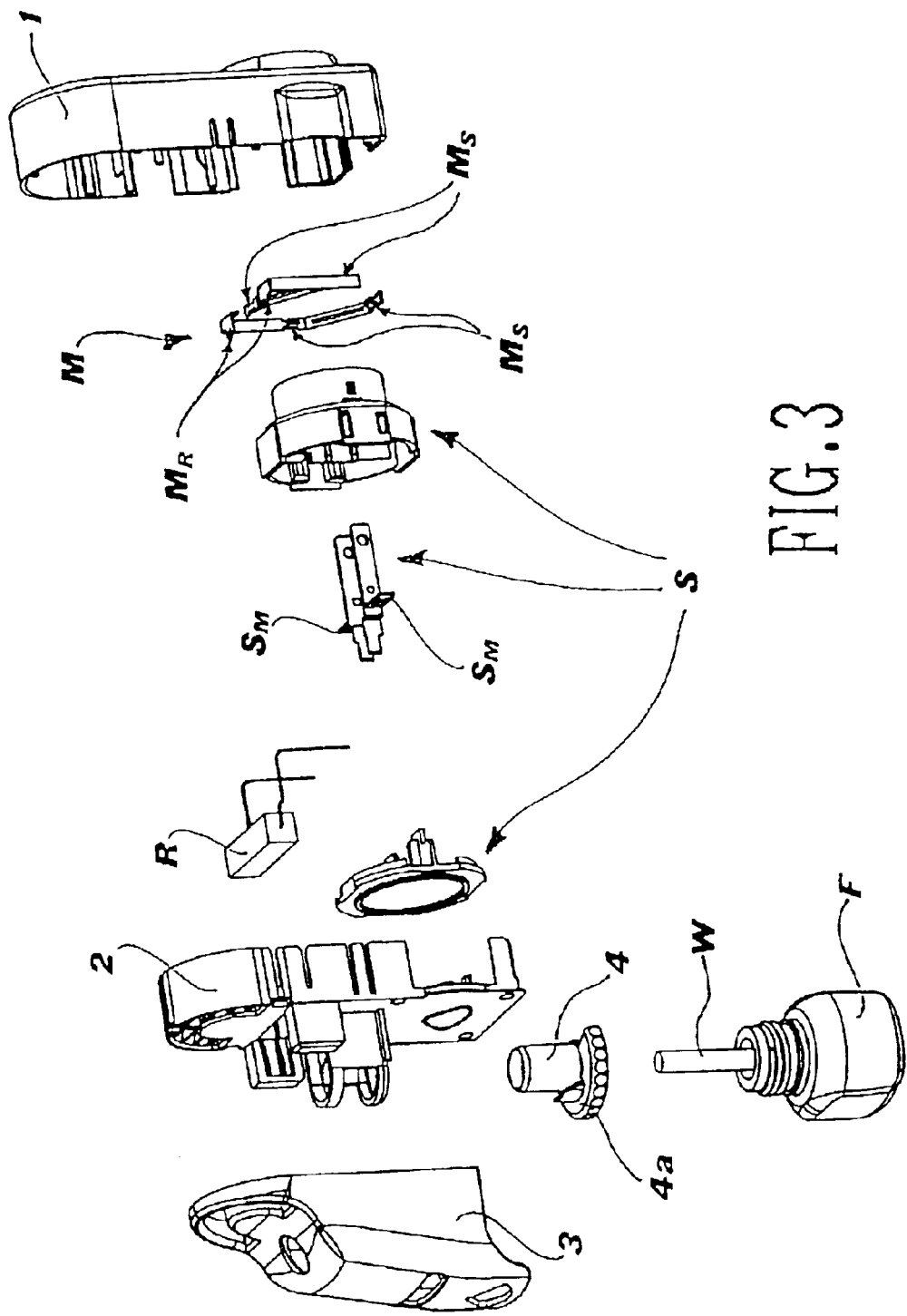
FIG. 3 is an exploded view of the vaporizer shown in FIGS. 1 and 2.

FIG. 3 illustrates a vaporizer including a draft regulator as an additional functional device. The draft regulator comprises a tube 4 with a partially removed wall (as more clearly shown in FIG. 8) and a dial 4a. The tube 4 and the dial 4a are supported within the second shell 2. The wick W extends through the inside of the tube 4, and the dial 4a is accessible through a window in the cover 3. The portion of the wick W directly exposed to the heating device R can be varied by rotating the dial 4a, thereby varying the rate at which the liquid substance is released to the ambient. A similar function can also be achieved through the use of a wick adjustment mechanism (not shown in the drawings), such as disclosed in co-pending U.S. patent application Ser. No. 09/916,275, the disclosure of which is incorporated herein by reference. Such a wick adjustment mechanism utilizes a cam device to laterally displace the wick, thereby varying the distance between the wick and the heating device. A draft regulator and a wick adjustment mechanism can be used together or as alternatives to each other.

Figure 4:
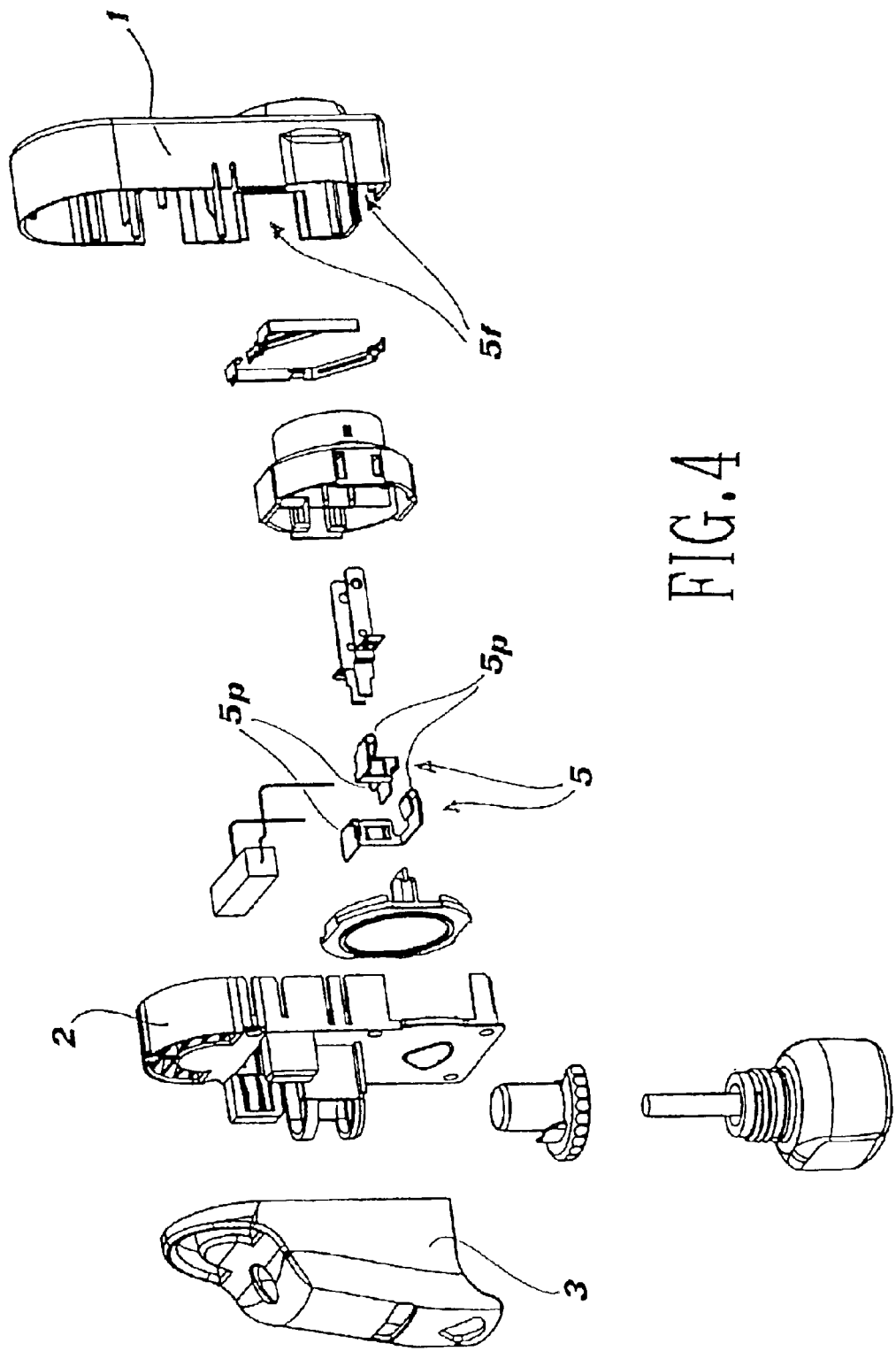
FIG. 4 is a view, similar to that of FIG. 3, in which the vaporizer is provided with an extra electrical socket.

FIG. 4 illustrates a vaporizer having an extra electrical socket. In this embodiment, a pair of metal strips 5 is provided within the body of the rotating plug assembly S. One end of each strip 5 is press-fitted into engagement with spring contacts on the pins of the plug, while the other end has a clamping system 5p for connecting to an electrical plug. The extra electrical socket is accessible via either of two windows 5f provided in the first shell 1, depending on the position assumed by the plug assembly S.

Figure 5:
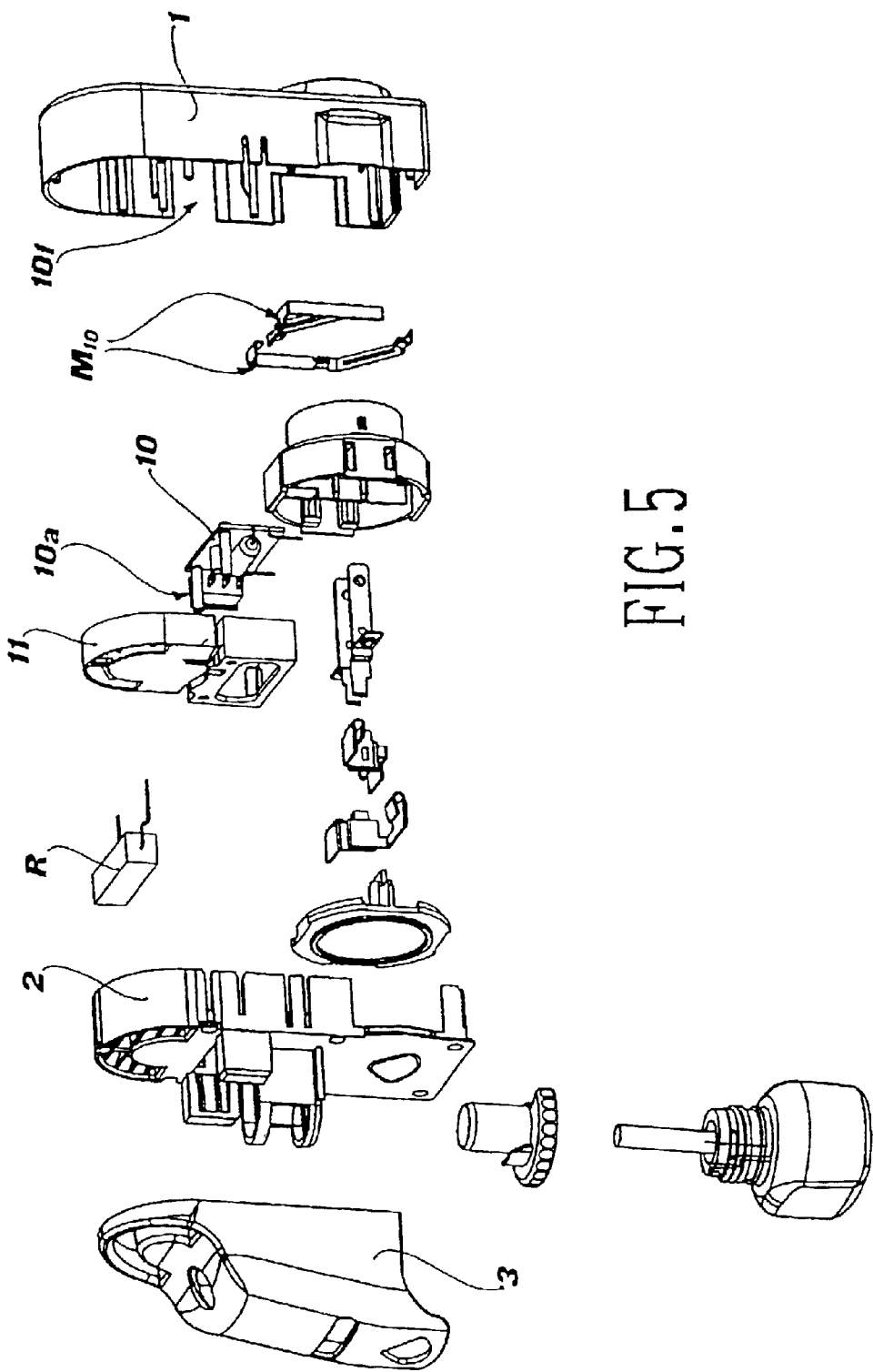
FIG. 5 is a view, similar to that of FIG. 4, in which the vaporizer is provided with an additional functional device, namely, a fan.

FIG. 5 illustrates a vaporizer including a fan as an additional functional device. The fan is housed in the top part of the first and second shells 1 and 2, which are provided, for this purpose, with a wide cavity. This cavity houses a printed electrical circuit 10 and a fan assembly 11 that is powered and controlled by the circuit 10. The circuit 10 is in turn powered by means of a pair of contacts $M_{10}$ (which is precisely the same pair of contacts $M_R$ described above in connection with FIG. 3). In this embodiment, the heating device R is connected to the circuit 10 instead of directly to the contact carrier M. The circuit 10 is equipped with a switch 10a that is accessible through a window 10f in the first shell 1.

Figure 6:
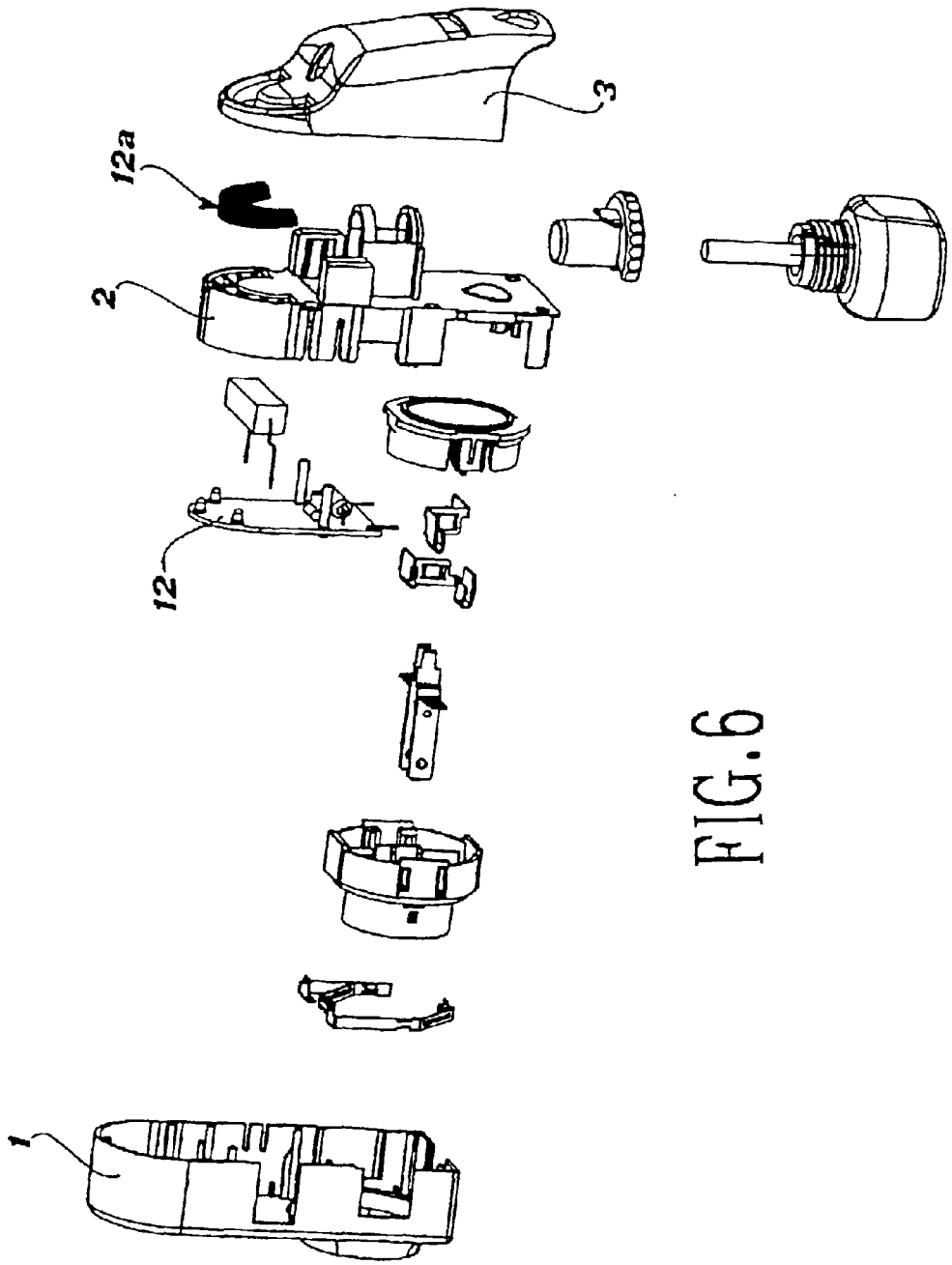
FIG. 6 is a view, similar to that of FIG. 4, but from a different viewpoint, in which the vaporizer is provided with an additional functional device, namely, a night light.

FIG. 6 illustrates a vaporizer including a night light 12 as an additional functional device. The night light 12 may be chosen from among various well-known types of commercially-available devices, such as incandescent lamps, neon lamps, LED devices (as shown in FIG. 6), or the like. If desired, a diffusing lens 12a may also be utilized. The electrical connections in this embodiment are identical to those discussed above with respect to FIG. 5.

Figure 7:
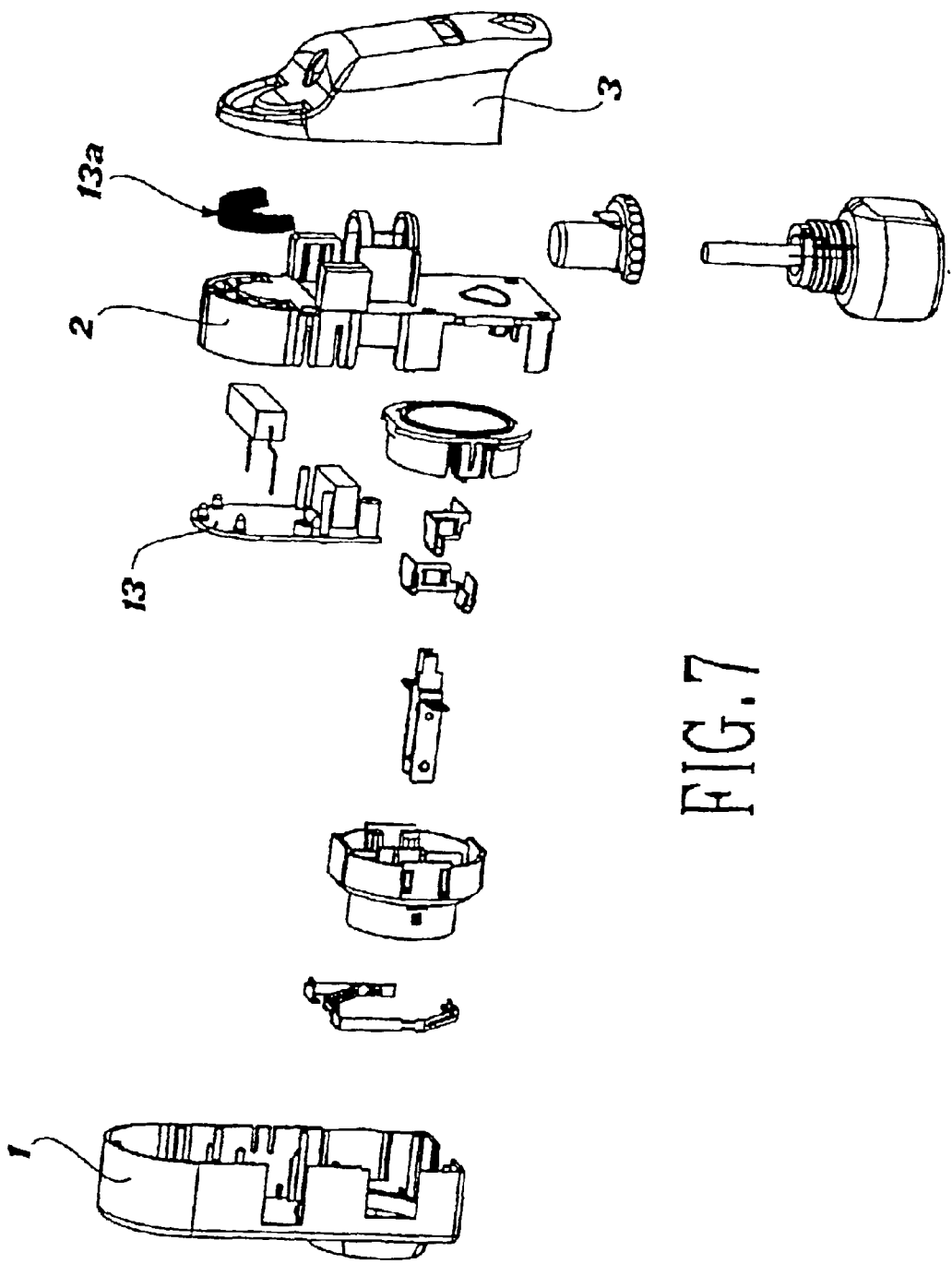
FIG. 7 is a view similar to that of FIG. 6, in which the vaporizer is provided with an indicator light as an additional functional device, instead of the night light.

FIG. 7 illustrates a vaporizer including a programmable user interface 13 as an additional functional device. In the preferred embodiment shown in FIG. 7, the interface includes three LED devices. The LED devices preferably have a much lower wattage than those used in the night light embodiment, because they are not intended to provide illumination, but rather only signal the different operating modes of the vaporizer. A diffusing lens 13a may also be used in this embodiment, if desired. The electrical connections in this embodiment are identical to those discussed above with respect to FIG. 5.

From the foregoing description, it should be clear that it is possible to modify the number and type of additional functional devices the vaporizer is equipped with without making any significant modification to its core housing structure, including the first and second shells 1 and 2. Instead, the vaporizer can simply be provided with a cover 3 having the desired aesthetic characteristics and only those access windows that are necessary based on the particular additional functional devices that the vaporizer is equipped with. During manufacture of the vaporizer, the additional functional devices are easily inserted into their respective places and connected to the electrical contacts already provided in the first and second shells 1 and 2.

Figure 8:
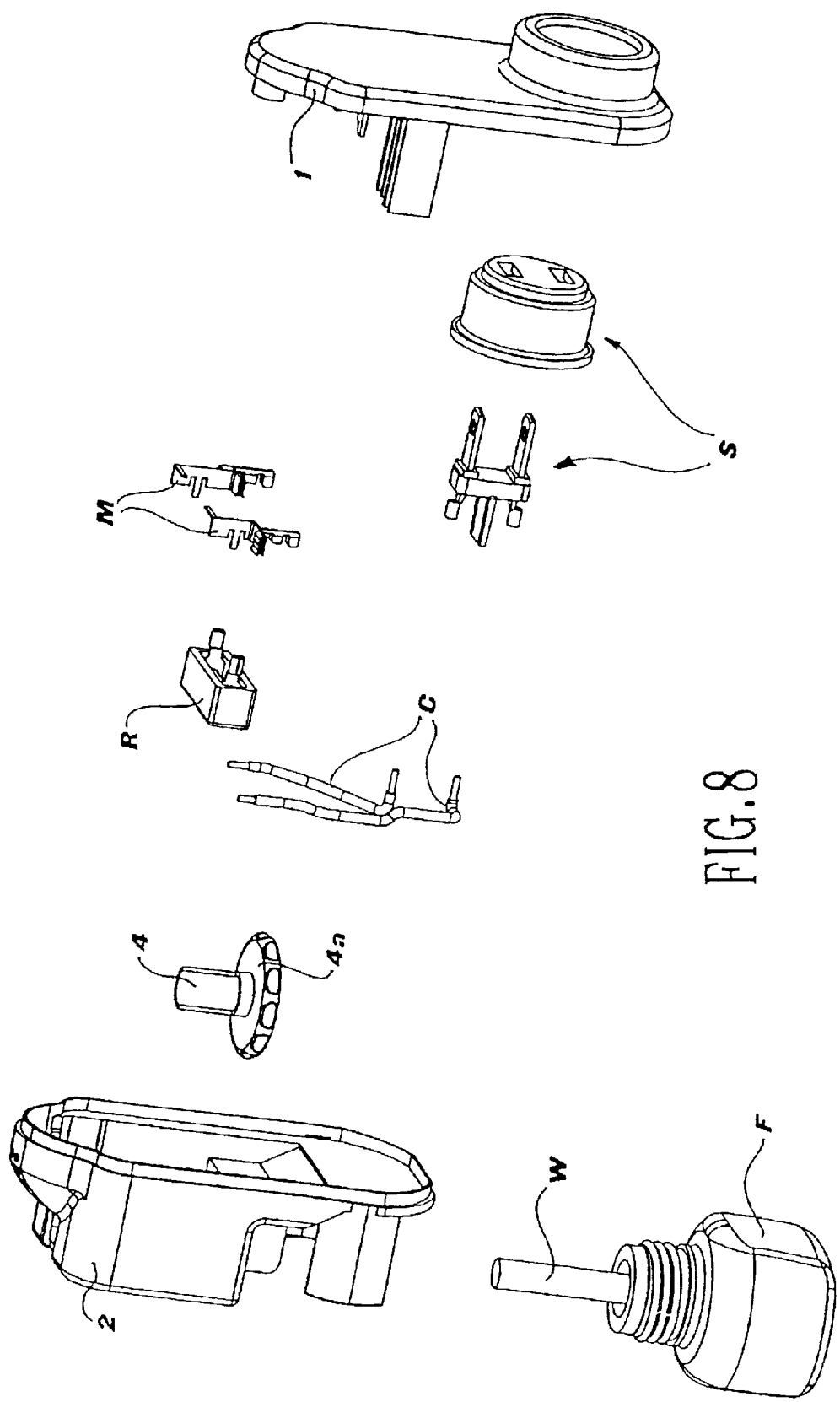
FIG. 8 illustrates a vaporizer according to a second preferred embodiment of our invention, where, for clarity, the cover has been omitted.
Figure 9:
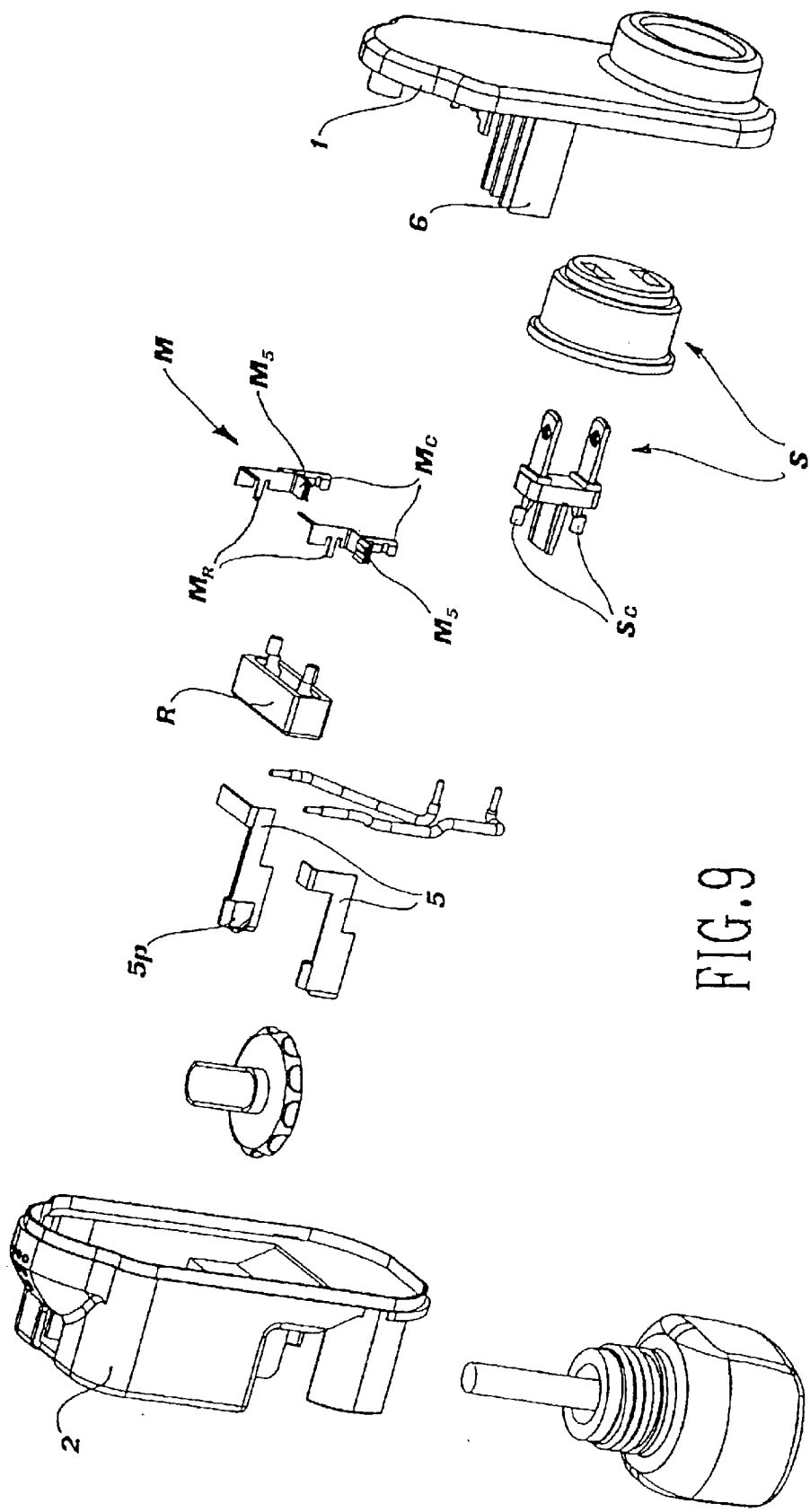
FIG. 9 is a view of the vaporizer shown in FIG. 8, provided with an extra electrical outlet.
Figure 10:
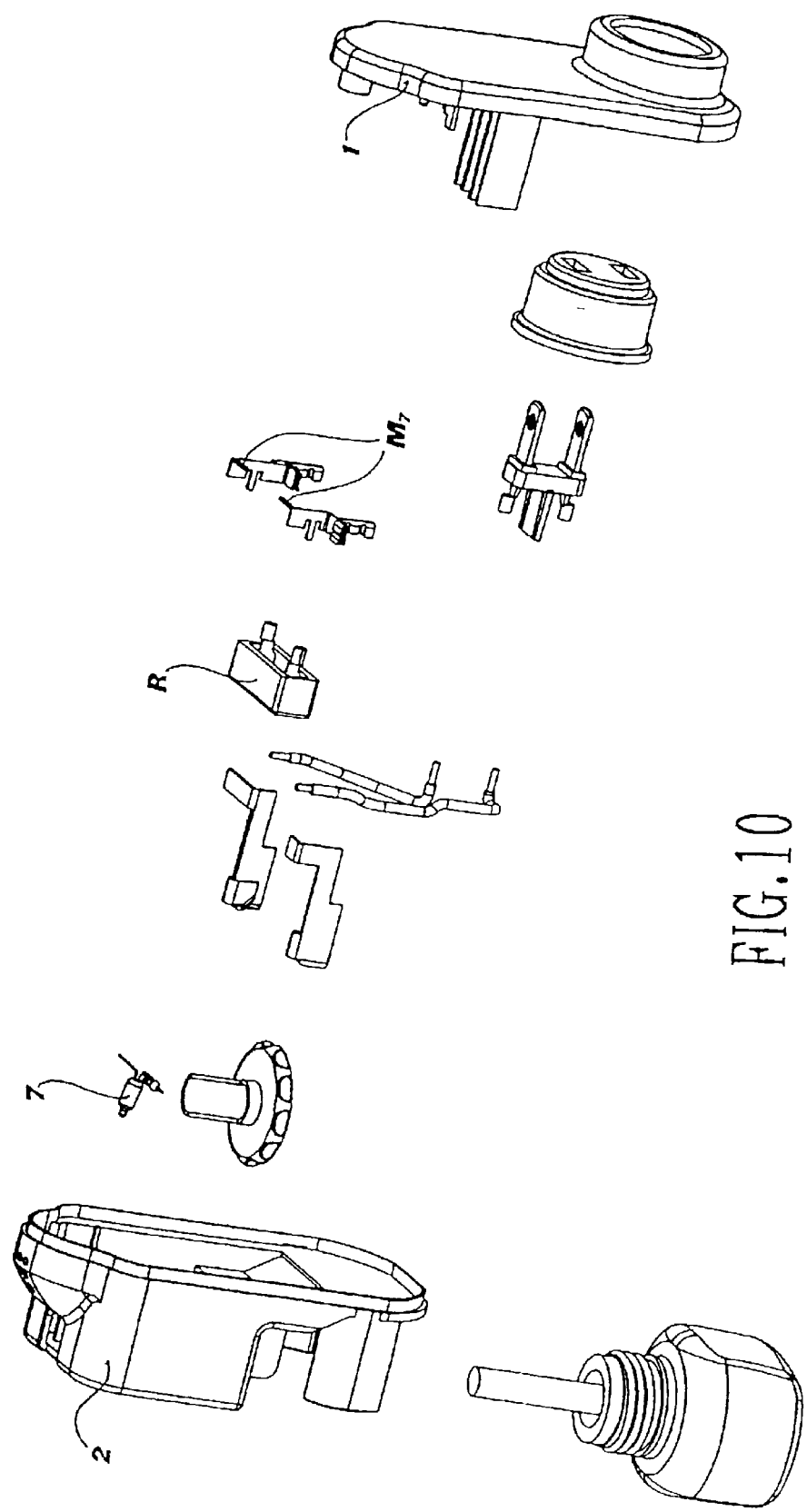
FIG. 10 is a view of the vaporizer shown in FIG. 9, provided with an additional functional device, namely, an indicator light.

FIGS. 8–10 illustrate a vaporizer according to a second preferred embodiment of our invention. This vaporizer includes elements similar to those described above with respect to the first preferred embodiment. Again, the vaporizer comprises a first shell 1 and a second shell 2 that are joined together to form the core housing structure of the vaporizer. The vaporizer also includes a cover, which is not illustrated in FIGS. 8–10 for the sake of clarity. As in the first preferred embodiment, the vaporizer includes a rotatable electrical plug assembly S, a contact carrier M having several electrical contacts, an electrical heating device R, a bottle F containing the liquid substance to be evaporated, and a wick W for drawing the liquid substance out of the bottle and toward an upper portion of the wick. In this embodiment, a pair of flexible electrical cables C connects contacts $S_C$ of the plug assembly S (shown in FIG. 9) to contacts $M_C$ on the contact carrier M. As with the first preferred embodiment, a number of additional functional devices may also be incorporated in the vaporizer shown in FIGS. 8–10.

FIG. 8, for example, illustrates a vaporizer including a draft regulator, similar to that described above with respect to FIG. 3, as an additional functional device.

FIG. 9, meanwhile, illustrates a vaporizer having an extra electrical socket. In this embodiment, a pair of metal strips 5 is carried by supports 6 formed on the inside of the first shell 1. One end of each strip 5 is press-fitted into engagement with spring contacts $M_5$ on the contact carrier M, and the other end of the strip 5 has a clamping system 5p for connecting to an electrical plug. The extra electrical socket is accessible via a window provided in the front of the second shell 2.

FIG. 10 illustrates a vaporizer including an indicator light 7 as an additional functional device. The indicator light 7 preferably comprises a neon lamp 7 seated adjacent to a window of the second shell 2. The lamp includes contacts that are press-fitted into engagement with spring contacts $M_7$ on the contact carrier M.

As those skilled in the art will appreciate, the vaporizer can be equipped with any number of these and other additional functional devices. Such devices can be inserted or removed from the vaporizer as desired, and none the devices is electrically or mechanically dependent on any of the other devices.

Figure 11:
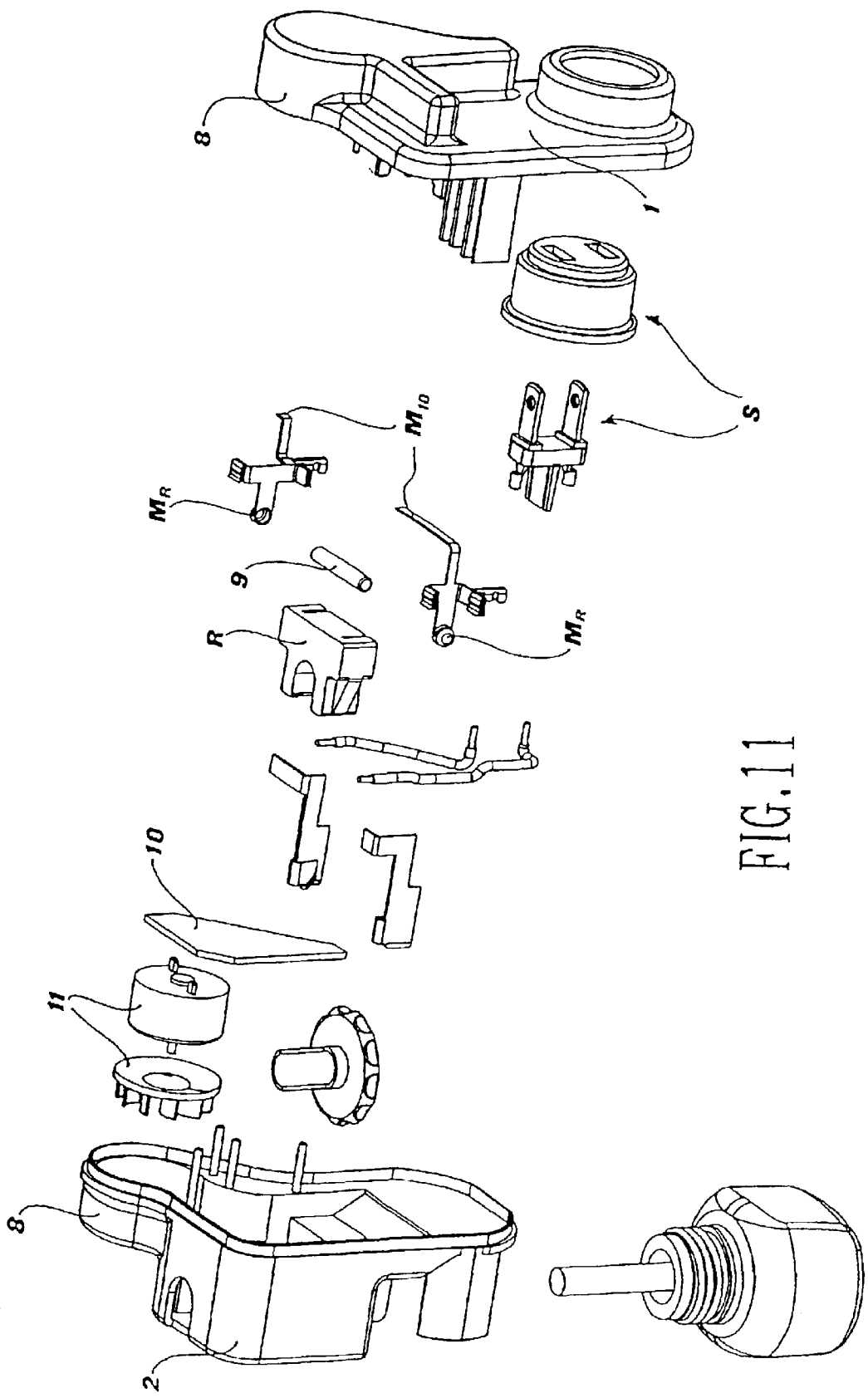
FIG. 11 illustrates a vaporizer according to a third preferred embodiment of our invention, provided with an additional functional device, namely, a fan. For clarity, the cover has been omitted in FIG. 11.
Figure 12:
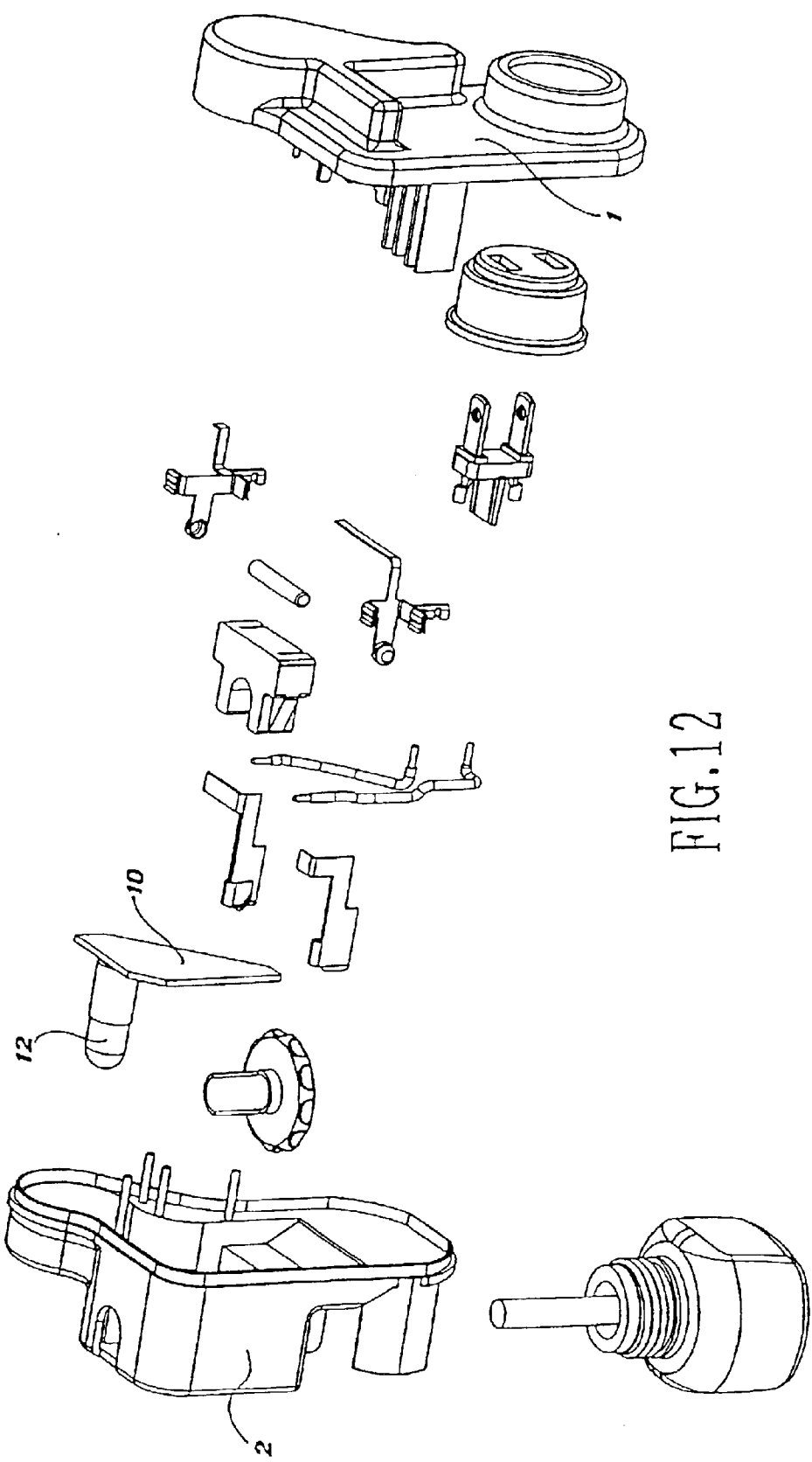
FIG. 12 illustrates a vaporizer similar to that illustrated in FIG. 11, in which the fan is replaced by a different additional functional device, namely, a night light.
Figure 13:
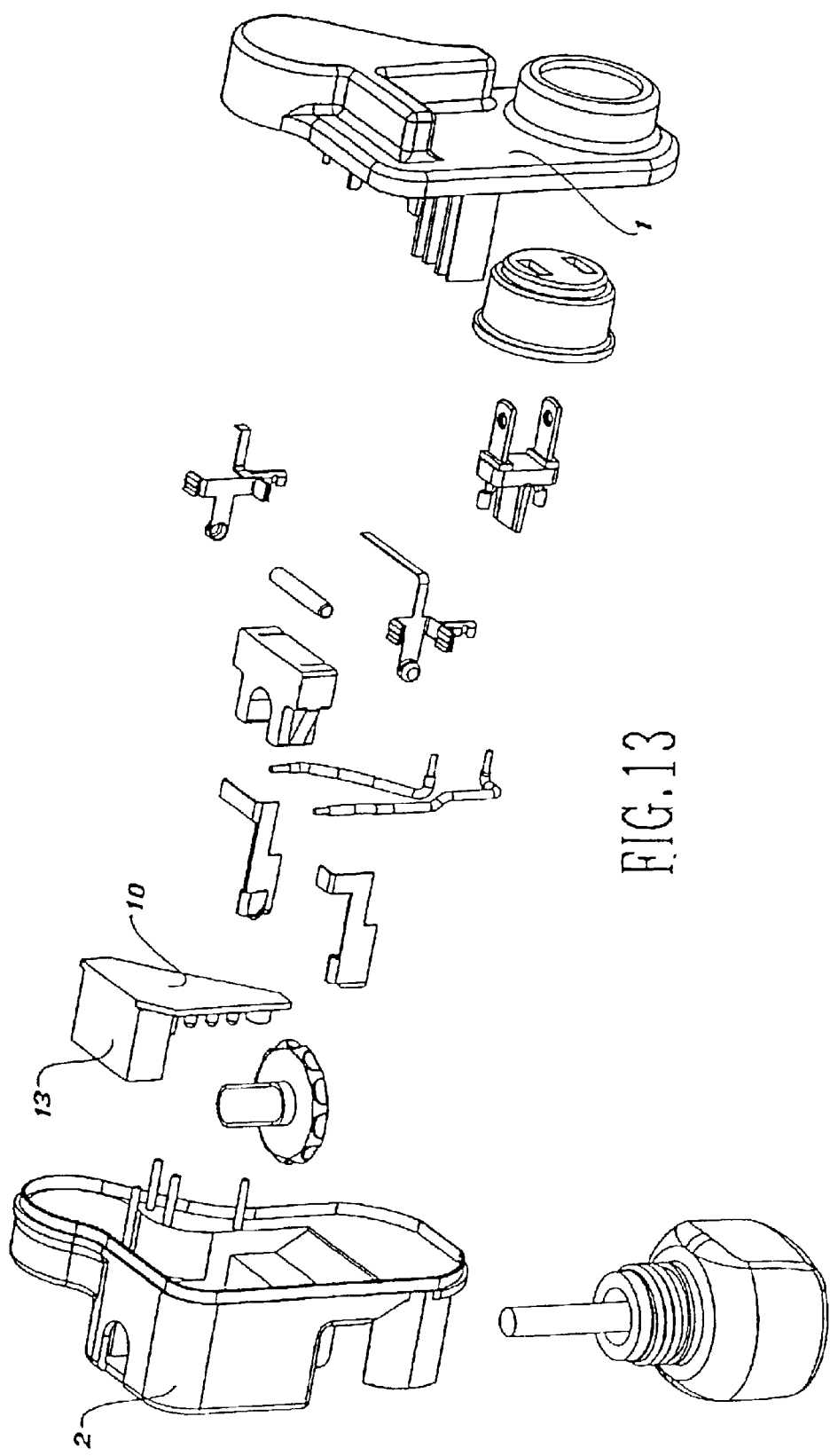
FIG. 13 illustrates a vaporizer similar to that illustrated in FIG. 11, in which the fan is replaced by a different additional functional device, namely, a programmable user surface.

Finally, FIGS. 11–13 illustrate a vaporizer according to a third preferred embodiment of our invention. This vaporizer includes elements similar to those described above with respect to the first and second preferred embodiments. In this embodiment, however, the first and second shells 1 and 2 include an expanded section 8 for housing complex and/or bulky additional functional devices.

In this embodiment, the heating device R includes a U-shaped portion that surrounds the wick W. A resistor 9 is held within a cavity in the heating device R by a pair of opposing contacts $M_R$ on contact carrier M. The heating device R may comprise any of several well-known heating elements.

In this embodiment, the vaporizer also comprises, in addition to the basic functions noted above, an extra electrical socket and a draft regulator. Other additional functional devices can be housed inside the expanded section 8. Such devices may include a fan 11 (as shown in FIG. 11), a night light 12 (as shown in FIG. 12), and/or a programmable user interface 13 (as shown in FIG. 13). Each additional functional device is powered by means of a printed electrical circuit 10, which is preferably contained within a lower part of the expanded section 8. The circuit 10 is in turn connected to contacts $M_{10}$ on the contact carrier M.

Our invention thus provides a vaporizer having a universal core housing structure that can be equipped with both basic functional features and one or more additional functional devices, without the need to substantially modify the housing structure itself. Meanwhile, a decorative outer cover, which is provided with access windows corresponding to whatever additional functional device(s) the vaporizer is equipped with, is substantially the only part of the vaporizer that is visible when looking at the vaporizer head-on.

The embodiments discussed above are representative of preferred embodiments of the present invention and are provided for illustrative purposes only. They are not intended to limit the scope of the invention. Although specific structures, components, circuits, etc., have been shown and described, such are not limiting. Modifications and variations are contemplated within the scope of the present invention, which is intended to be limited only by the scope of the accompanying claims.

Industrial Applicability

Our invention relates to a multi-functional vaporizer for use in connection with liquid substances, such as aromatic liquids, insecticides, or the like. In addition to performing the basic function of vaporizing the liquid substance by means of an electrical heating device, the vaporizer can easily and economically be equipped with one or more additional functional devices, such as a draft regulator, a wick adjustment mechanism, a fan, a night light, an indicator light, a programmable user interface, or the like.

We claim:

1. A multi-functional electrical vaporizer for a liquid substance, the vaporizer comprising:

a bottle for holding a liquid substance;

a wick for drawing the liquid substance out of the bottle, the wick having a lower portion disposed within the bottle and an upper portion extending out of the bottle;

an electrical heating device positioned proximate to the upper portion of the wick;

an electrical plug assembly;

an electrical circuit, connected between the electrical plug assembly and the electrical heating device, for powering the electrical heating device;

a housing structure with respect to which the bottle is detachably secured and in which at least the electrical plug assembly, the electrical circuit, and the electrical heating device are disposed, the housing structure including a first shell and a second shell that are joined together; and a cover that is joined to and at least partially covers the housing structure, wherein the housing structure is configured to receive any of a plurality of different additional functional devices, the cover is provided with at least one access window corresponding to whatever additional functional device the housing structure is to be equipped with, and the bottle is detachably secured within a space defined between an outer surface of the housing structure and an inner surface of the cover.

2. The vaporizer of claim 1, wherein at least some of the plurality of additional functional devices are electrical, and the electrical circuit of the vaporizer includes at least one electrical connection for connecting any of the electrical additional functional devices thereto.

3. The vaporizer of claim 1, wherein the electrical circuit of the vaporizer includes flexible cables connected between the electrical plug assembly and the electrical heating device.

4. The vaporizer of claim 1, wherein the electrical plug assembly includes a plug that is rotatable through a range of 360°.

5. The vaporizer of claim 1, wherein the plurality of different additional functional devices includes at least two of the following: (i) a draft regulator, (ii) a wick adjustment mechanism for displacing the wick relative to the electrical heating device, (iii) a fan, (iv) a night light, (v) an indicator light, and (vi) a programmable user interface.

6. A multi-functional electrical vaporizer for dispersing a liquid substance contained in a bottle provided with a wick for drawing the liquid substance out of the bottle and toward an upper portion of the wick, the vaporizer comprising:

an electrical heating device for being positioned proximate to the upper portion of the wick;

an electrical plug assembly;

an electrical circuit, connected between the electrical plug assembly and the electrical heating device, for powering the electrical heating device;

a housing structure in which at least the electrical plug assembly, the electrical circuit, and the electrical heating device are disposed, the housing structure including a first shell and a second shell that are joined together, the housing structure being configured to receive any of a plurality of different types of additional functional devices, including at least two different ones of the following types: (i) a fan, (ii) a light, and (iii) a programmable user interface;

at least one additional functional device selected from among the plurality of different types of additional functional devices, disposed within the housing structure; and a cover that is joined to and at least partially covers the housing structure, the cover including at least one access window corresponding to the additional functional device the housing structure is equipped with, wherein an outer surface of the housing structure and an inner surface of the cover define a space within which the bottle can be detachably secured.

7. The vaporizer of claim 6, wherein the additional functional device that the housing structure is equipped with is electrical, and the electrical circuit of the vaporizer includes at least one electrical connection for connecting the electrical additional functional device thereto.

8. The vaporizer of claim 6, wherein the electrical circuit of the vaporizer includes flexible cables connected between the electrical plug assembly and the electrical heating device.

9. The vaporizer of claim 6, wherein the electrical plug assembly includes a plug that is rotatable through a range of 360°.

10. The vaporizer of claim 6, wherein the additional functional device that the housing structure is equipped with is a fan, and the housing structure further includes a wick adjustment mechanism.

11. The vaporizer of claim 6, wherein the housing structure further includes a draft regulator.

12. The vaporizer of claim 6, wherein the housing structure further includes a wick adjustment mechanism for displacing the wick relative to the electrical heating device.

13. The vaporizer of claim 12, wherein the additional functional device that the housing structure is equipped with is a light.

14. A method of manufacturing a plurality of electrical vaporizers having a common core housing structure and different features, the method comprising the following steps:

forming a plurality of core housing structures, each including joinable first and second shells and each, being configured to receive any of a plurality of different types of additional functional devices, including at least two different ones of the following types: (i) a fan, (ii) a light, and (iii) a programmable user interface;

disposing within each core housing structure an electrical plug assembly, an electrical heating device, and an electrical circuit that is connected between the electrical plug assembly and the electrical heating device;

equipping respective ones of the plurality of core housing structures with different ones of the plurality of different types of additional functional devices, without substantially modifying the core housing structure; and providing each core housing structure with a cover, the cover including at least one access window corresponding to the additional functional device the core housing structure is equipped with.

15. The method of claim 14, wherein the equipping step involves equipping at least one of the plurality of core the housing structures with a fan, and further includes equipping that same core housing structure with a wick adjustment mechanism.

16. The method of claim 14, further comprising a step of detachably securing a bottle containing the liquid substance within a space defined by an outer surface of each core housing structure and an inner surface of each cover.

17. The method of claim 14, wherein the equipping step further involves equipping at least one of the plurality of core housing structures with a draft regulator.

18. The method of claim 14, wherein the equipping step further involves equipping at least one of the plurality of core housing structures with a wick adjustment mechanism for displacing the wick relative to the electrical heating device.

19. The method of claim 18, wherein the equipping step involves equipping at least one of the plurality of core housing structures with a light.

* * * * *